United States Patent
Jing et al.

(10) Patent No.: US 8,416,915 B2
(45) Date of Patent: *Apr. 9, 2013

(54) FULL FIELD MAMMOGRAPHY WITH TISSUE EXPOSURE CONTROL, TOMOSYNTHESIS, AND DYNAMIC FIELD OF VIEW PROCESSING

(75) Inventors: Zhenxue Jing, Southbury, CT (US); Georgia Hitzke, Saunderstown, RI (US); Donald Kennedy, Bethel, CT (US); Andrew Smith, Medford, MA (US); Jay A. Stein, Boston, MA (US)

(73) Assignee: Hologic, Inc., Bedford, MA (US)

( * ) Notice: Subject to any disclaimer, the term of this patent is extended or adjusted under 35 U.S.C. 154(b) by 2 days.

This patent is subject to a terminal disclaimer.

(21) Appl. No.: 13/111,618

(22) Filed: May 19, 2011

(65) Prior Publication Data

US 2011/0216879 A1 Sep. 8, 2011

Related U.S. Application Data

(63) Continuation of application No. 12/699,613, filed on Feb. 3, 2010, now Pat. No. 7,949,091, which is a continuation of application No. 12/233,240, filed on Sep. 18, 2008, now Pat. No. 7,760,853, which is a continuation of application No. 11/582,061, filed on Oct. 16, 2006, now Pat. No. 7,430,272, which is a continuation of application No. 10/305,480, filed on Nov. 27, 2002, now Pat. No. 7,123,684.

(51) Int. Cl.
*A61B 6/04* (2006.01)

(52) U.S. Cl. .............................. 378/37; 378/21

(58) Field of Classification Search ............... 378/21, 378/22, 37
See application file for complete search history.

(56) References Cited

U.S. PATENT DOCUMENTS

| 3,502,878 A | 3/1970 | Stewart |
|---|---|---|
| 3,863,073 A | 1/1975 | Wagner |
| 3,971,950 A | 7/1976 | Evans et al. |

(Continued)

FOREIGN PATENT DOCUMENTS

| EP | 0775467 A1 | 5/1997 |
|---|---|---|
| EP | 0982001 A1 | 3/2000 |

(Continued)

OTHER PUBLICATIONS

Kita et al., "Correspondence between different view breast X-rays using simulation of breast deformation", Proceedings 1998 IEE Computer Society Conference on Computer Vision and Pattern Recongnition, Santa Basbara, CA, Jun. 23-25, 1998, pp. 700-707.

(Continued)

*Primary Examiner* — Glen Kao
(74) *Attorney, Agent, or Firm* — Cooper & Dunham LLP

(57) ABSTRACT

A mammography system using a tissue exposure control relying on estimates of the thickness of the compressed and immobilized breast and of breast density to automatically derive one or more technic factors. The system further uses a tomosynthesis arrangement that maintains the focus of an anti-scatter grid on the x-ray source and also maintains the field of view of the x-ray receptor. Finally, the system finds an outline that forms a reduced field of view that still encompasses the breast in the image, and uses for further processing, transmission or archival storage the data within said reduced field of view.

9 Claims, 4 Drawing Sheets

U.S. PATENT DOCUMENTS

| | | |
|---|---|---|
| 4,160,906 A | 7/1979 | Daniels et al. |
| 4,310,766 A | 1/1982 | Finkenzeller et al. |
| 4,496,557 A | 1/1985 | Malen et al. |
| 4,513,433 A * | 4/1985 | Weiss et al. ............... 378/23 |
| 4,559,641 A | 12/1985 | Caugant et al. |
| 4,706,269 A | 11/1987 | Reina et al. |
| 4,744,099 A | 5/1988 | Huettenrauch et al. |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,889 A | 9/1997 | Hara |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,970,118 A * | 10/1999 | Sokolov ............... 378/155 |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields et al. |
| 6,501,819 B2 | 12/2002 | Unger et al. |
| 6,556,655 B1 | 4/2003 | Chichereau et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,940,943 B2 | 9/2005 | Claus et al. |
| 6,978,040 B2 | 12/2005 | Berestov |
| 6,999,554 B2 | 2/2006 | Mertelmeier |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,245,694 B2 | 7/2007 | Jing et al. |
| 7,315,607 B2 | 1/2008 | Ramsauer |
| 7,319,735 B2 | 1/2008 | Defreitas et al. |
| 7,323,692 B2 | 1/2008 | Rowlands et al. |
| 7,430,272 B2 | 9/2008 | Jing et al. |
| 7,443,949 B2 | 10/2008 | Defreitas et al. |
| 7,630,533 B2 | 12/2009 | Ruth et al. |
| 7,760,853 B2 * | 7/2010 | Jing et al. ............... 378/37 |
| 2001/0038681 A1 | 11/2001 | Stanton et al. |
| 2002/0012450 A1 | 1/2002 | Tsujii |
| 2002/0050986 A1 | 5/2002 | Inoue et al. |
| 2002/0075997 A1 | 6/2002 | Unger et al. |
| 2003/0018272 A1 | 1/2003 | Treado et al. |
| 2003/0072417 A1 * | 4/2003 | Kaufhold et al. ............... 378/207 |
| 2003/0073895 A1 | 4/2003 | Nields et al. |
| 2003/0095624 A1 | 5/2003 | Eberhard et al. |
| 2003/0194050 A1 | 10/2003 | Eberhard et al. |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0066884 A1 | 4/2004 | Hermann Claus et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0105679 A1 | 5/2005 | Wu et al. |
| 2005/0113681 A1 | 5/2005 | DeFreitas et al. |
| 2005/0113715 A1 | 5/2005 | Schwindt et al. |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0130979 A1 | 6/2008 | Ren et al. |
| 2009/0003519 A1 | 1/2009 | Defreitas et al. |
| 2009/0010384 A1 | 1/2009 | Jing et al. |
| 2009/0080594 A1 | 3/2009 | Brooks et al. |

| | | | |
|---|---|---|---|
| 2009/0080602 | A1 | 3/2009 | Brooks et al. |
| 2009/0135997 | A1 | 5/2009 | Defreitas et al. |
| 2009/0268865 | A1 | 10/2009 | Ren et al. |

FOREIGN PATENT DOCUMENTS

| | | |
|---|---|---|
| EP | 1428473 A2 | 6/2004 |
| WO | WO 90/05485 | 5/1990 |
| WO | WO 98/16903 | 4/1998 |
| WO | WO 00/51484 | 9/2000 |
| WO | WO 03/020114 A2 | 3/2003 |
| WO | WO 2005/051197 A1 | 6/2005 |
| WO | WO 2005110230 A1 | 11/2005 |
| WO | WO 2005112767 A1 | 12/2005 |
| WO | WO 2006/055830 A2 | 5/2006 |
| WO | WO 2006/058160 A2 | 6/2006 |

OTHER PUBLICATIONS

Digital Clinical Reports, Tomosynthesis, GE Brochure 98-5493, Nov. 1998.

Mammographic Accreditation Phantom, http://www.cirsinc.com/pdfs/015cp.pdf, (2006).

Heang-Ping Chan et al., "ROC study of the effect of stereoscopic imaging on assessment of breast lesions", Medical Physics, vol. 32, No. 4, Apr. 2005.

Cole, Elodia, et al., "The Effects of Gray Scale Image Processing on Digital Mammography Interpretation Performance", *Academic Radiology*, vol. 12, No. 5, pp. 585-595, May 2005.

Federica Pediconi et al., "Color-coded automated signal intensity-curve for detection and characterization of breast lesions: Preliminary evaluation of a new software for MR-based breast imaging", International Congress Series 1281 (2005) 1081-1086.

"Essentials for life: Senographe Essential Full-Field Digital Mammography system", GE Health-care Brochure, MM-0132-05.06-EN-US, 2006.

Senographe 700 & 800T (GE); 2-page download on Jun. 22, 2006 from www.gehealthcare.com/inen/rad/whe/products/mswh800t.html.; Figures 1-7 on 4 sheets relateral shift compression paddle.

"Lorad Selenia" Document B-BI-SEO US/Intl (May 2006) copy right Hologic 2006.

"Filtered Back Projection," (Nygren) published May 8, 2007; URL: http://web.archive.org/web/19991010131715/http://www.owlnet.rice.edu/~elec539/Projects97/cult/node2.html.

Smith, A., "Fundamentals of Breast Tomosynthesis", White Paper, Hologic Inc., WP-00007, Jun. 2008.

U.S. Appl. No. 12/396,978 of Andrew Paul Smith et al., filed Mar. 3, 2009.

U.S. Appl. No. 12/491,147 of Georgia Hitzke et al. filed Jun. 24, 2009.

U.S. Appl. No. 12/507,450 of Baorui Ren et al., filed Jul. 22, 2009.

U.S. Appl. No. 12/535,343 of Baorui Ren et al., filed Aug. 4, 2009.

U.S. Appl. No. 12/539,460 of Nikolaos A. Gkanatsios et al., filed Aug. 11, 2009.

U.S. Appl. No. 12/541,715 of Zhenxue Jing et al., filed Aug. 14, 2009.

U.S. Appl. No. 12/605,031 of Chris Ruth et al., filed Oct. 23, 2009.

\* cited by examiner

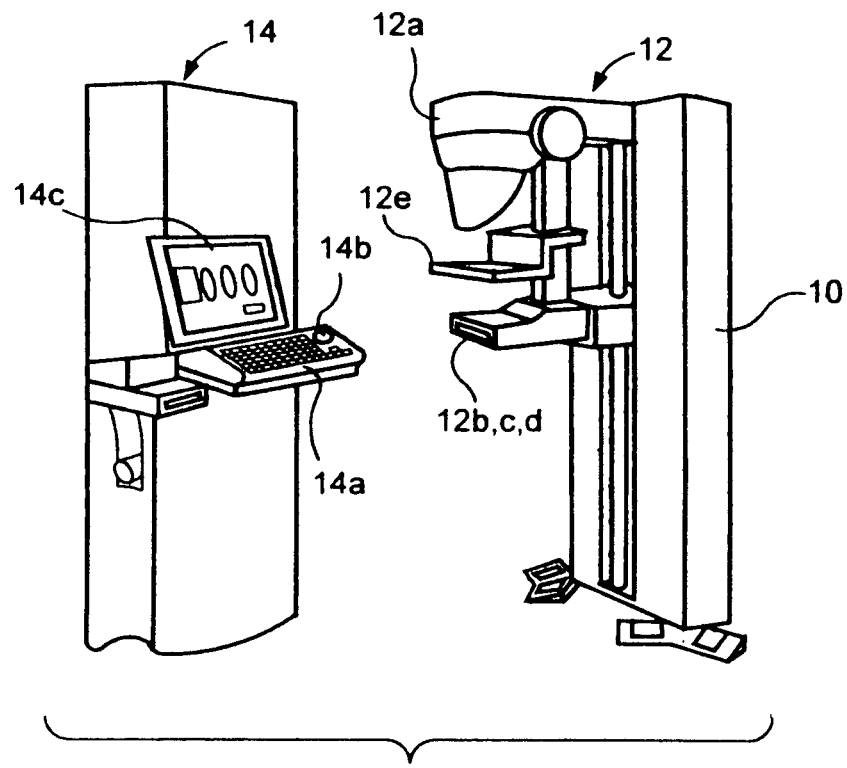
F I G. 1
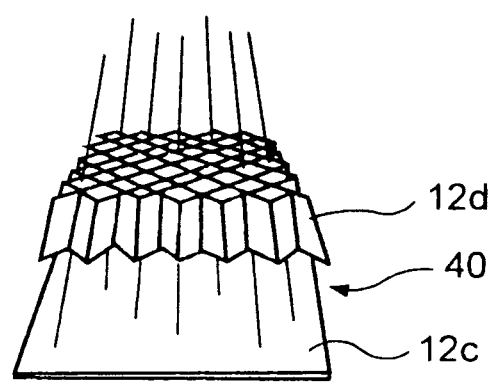
F I G. 3

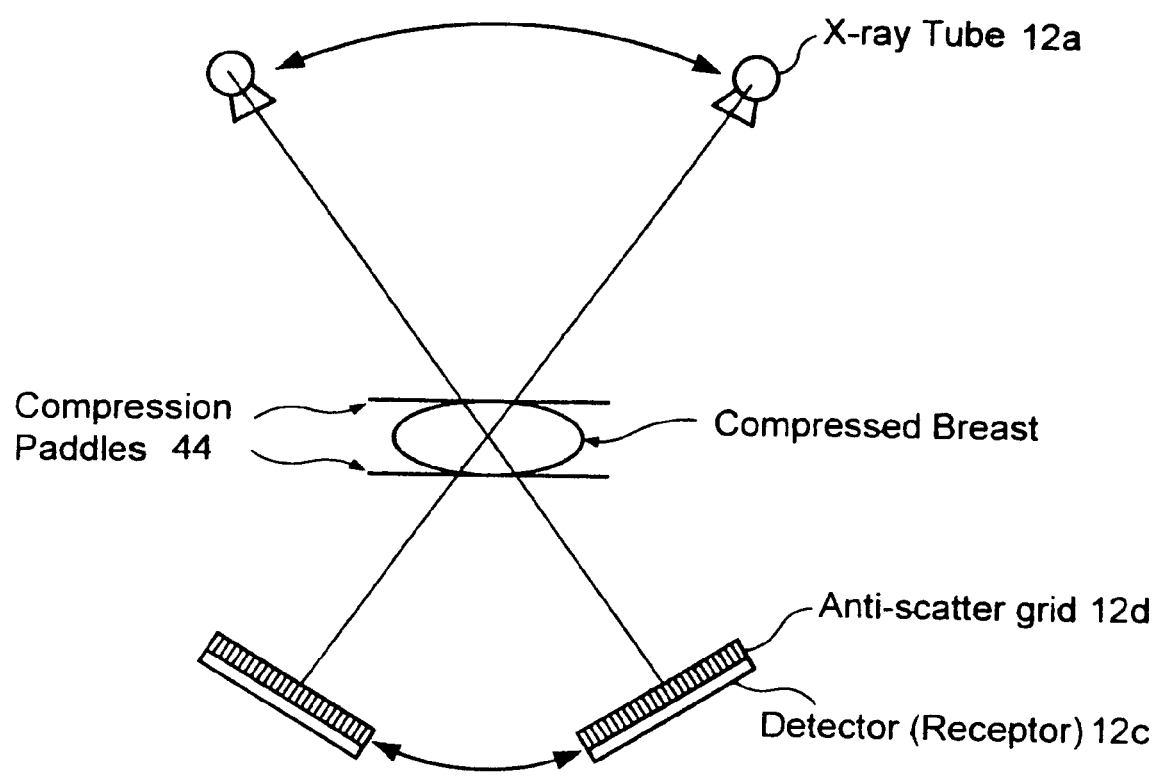
F I G. 4

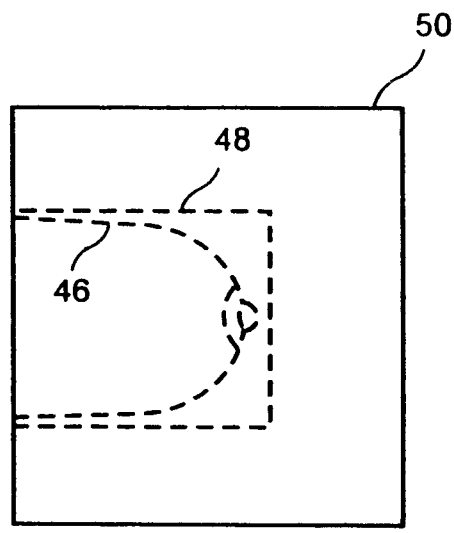
F I G. 5
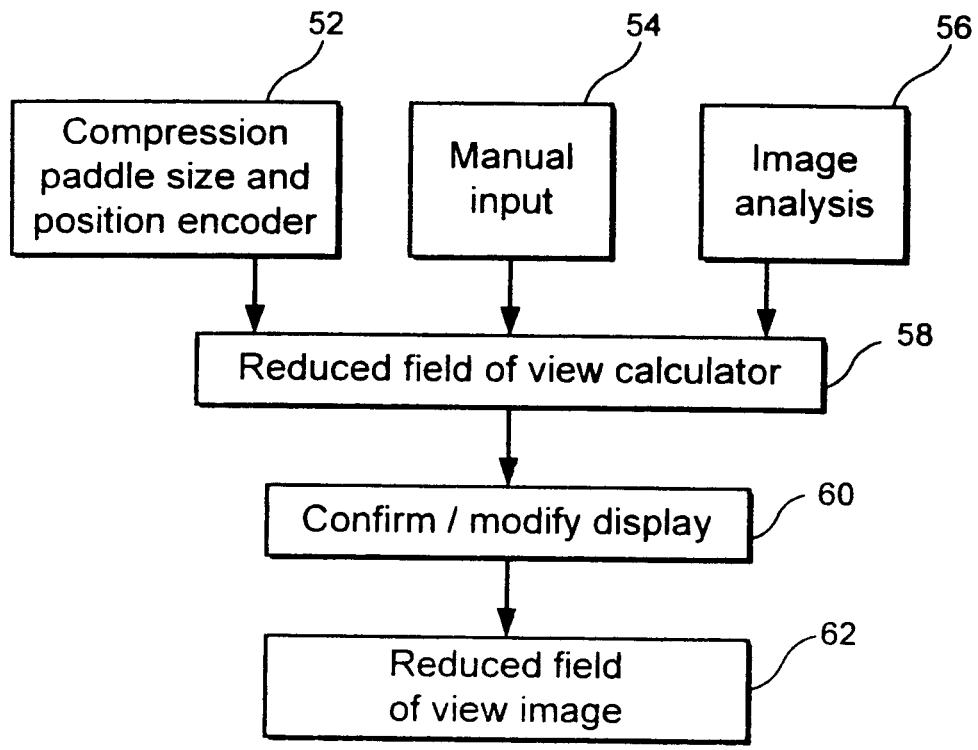
F I G. 6

FULL FIELD MAMMOGRAPHY WITH TISSUE EXPOSURE CONTROL, TOMOSYNTHESIS, AND DYNAMIC FIELD OF VIEW PROCESSING

CROSS-REFERENCE TO RELATED APPLICATIONS

This application is a Rule 1.53(b) Continuation of prior application Ser. No.: 12/699,613, filed on Feb. 3, 2010, now U.S. Pat. No. 7,949,091 which in turn is a Rule 1.53(b) continuation of application Ser. No. 12/233,240, filed on Sep. 18, 2008, now U.S. Pat. No. 7,760,853 which in turn is a Rule 1.53(b) continuation of application Ser. No. 11/582,061, filed on Oct. 16, 2006, now U.S. Pat. No. 7,430,272, which in turn is a Rule 1.53(b) continuation of application Ser. No. 10/305,480, filed on Nov. 27, 2002, now U.S. Pat. No. 7,123,684.

FIELD

This patent specification is in the field of mammography systems and methods, and is particularly applicable to using large field, flat panel, digital x-ray receptors.

BACKGROUND

X-ray mammography systems typically use an x-ray source mounted at one end of a rotatable c-arm assembly and an image receptor at the other. Between the x-ray source and the image receptor is a device for compressing and immobilizing a breast. Until recently, the image receptor was typically a screen-film cassette, which generated an image related to the detected transmission of x-rays through the breast. The device for compressing the breast against the image receptor, or a breast tray covering the receptor, is often called a paddle, and comes in a variety of sizes to match both the cassette size and the breast size. Such matching is desirable because the use of a small size paddle on a large breast can result in uneven and inadequate breast compression and may not allow full-breast imaging, while using a large paddle on a small breast can impede access to the breast, which is important during the compression cycle in order to optimize the amount of breast tissue brought into the field of view of the image receptor.

New mammography systems are now being introduced to use digital image receptors in place of screen-film, and have many well recognized advantages. Such a system is currently available from the assignee hereof under the trade name Selenia. Further information thereon, found at www.loradmedical.com/selenia, is hereby incorporated by reference in this disclosure. The Selenia system uses a digital flat panel detector made by the Digital Radiography Corp. division of the assignee hereof, located in Newark, Delaware. The panel has a 24×29 cm field of view. Various other aspects of a mammography system and method are describe in commonly assigned provisional Patent Application Ser. No. 60/350,213 filed Oct. 19, 2001 and International Application No. PCT/US02/33058 filed Oct. 17, 2002, which is hereby incorporated by reference.

Mammography systems often have provisions for partly or fully automating the selection of appropriate technic factors for an x-ray exposure, such as one or more of kVp (the x-ray tube accelerating potential), mA (x-ray tube current), and exposure time. When a film-screen image receptor is used, this can be done by relying on exposure detectors at the other side of the film from the x-ray source. An imaging exposure of the breast is stopped when these exposure detectors indicate that they have received a sufficient amount of x-radiation. This is not believed practical for use with flat panel image receptors for a number of reasons. Accordingly, one known approach for use with digital flat panel image receptors is to take a short, low x-ray dosage pre-exposure after the breast has been compressed, and then take an imaging exposure while the breast remains immobilized, using technic factors based on measurements taken with the same receptor in the pre-exposure.

Another aspect of mammography is proposals for tomographic imaging or tomosynthesis. In principle, a tomographic image of a plane in the breast can be obtained by moving at least one of the x-ray source and the image receptor relative to the breast during the x-ray exposure. If the x-ray source and the image receptor move in opposite directions in parallel planes, with the appropriate geometry, a plane in the breast that is parallel to the image receptor remains in focus during the entire exposure while the images of all other planes in the breast are blurred and become background noise in the final image. One known approach is to keep the image receptor stationary but move the x-ray source in a path suitable for tomosynthesis. One problem with this is that this limits the field of view for the tomosynthesis image. Another is that this makes it difficult to effectively control the effects of scattered radiation as it becomes difficult to maintain the commonly used anti-scatter grids focused on the focal spot of the x-ray source. Yet another problem is that this arrangement allows for only relatively shallow (small) angles relative to a normal to the plane of the receptor.

Yet another aspect of mammography using flat panel digital image receptors is the transmission and storage of images. Many health facilities had image storage systems such as PACS, and protocols such as DICOM exist for formatting medical x-ray images for storage and future use. However, in many if not most cases, the breast takes up only a part of the image taken with flat panel digital receptors such that an imaginary rectangle that envelops the image of the breast is smaller than the field of view of the receptor. One proposal has been made for use with a fan beam of x-rays scanning a flat panel digital image receptor, and is believed to involve eliminating from storage image areas that do not contain an image of the breast. However, that proposal is believed to be specific to the use of a scanning fan beam of x-rays.

The system and method disclosed in this patent specification are designed to overcome these and other disadvantages of the known prior proposals. The cited patents are hereby incorporated by reference in this patent specification.

SUMMARY

An object of the disclosed system and method is to provide a particularly effective and advantageous exposure control for mammography using flat panel, digital x-ray receptors, using an estimate of the thickness of the compressed breast and of breast density.

Another object is to improve tomosynthesis in mammography, preferably while retaining the benefits of a focused anti-scatter grid and avoiding a reduction of the field of view.

Yet another object is to improve the efficiency of x-ray image storage and transmission, particularly for mammography images, by selective use of decreased effective image size.

BRIEF DESCRIPTION OF THE DRAWING

FIG. 1 illustrates a digital mammography system in which preferred embodiments disclosed herein can be implemented.

FIG. 3 illustrates a focused anti-scatter grid that can be used in the system of FIGS. 3 and 1.

FIG. 4 illustrates an aspect of tomosynthesis in mammography.

FIG. 5 illustrates selection of a decreased size mammography image for storage and transmission.

FIG. 6 illustrates processes involved in selecting a reduced size image for transmission and storage.

DETAILED DESCRIPTION OF PREFERRED EMBODIMENTS

Figure 2:
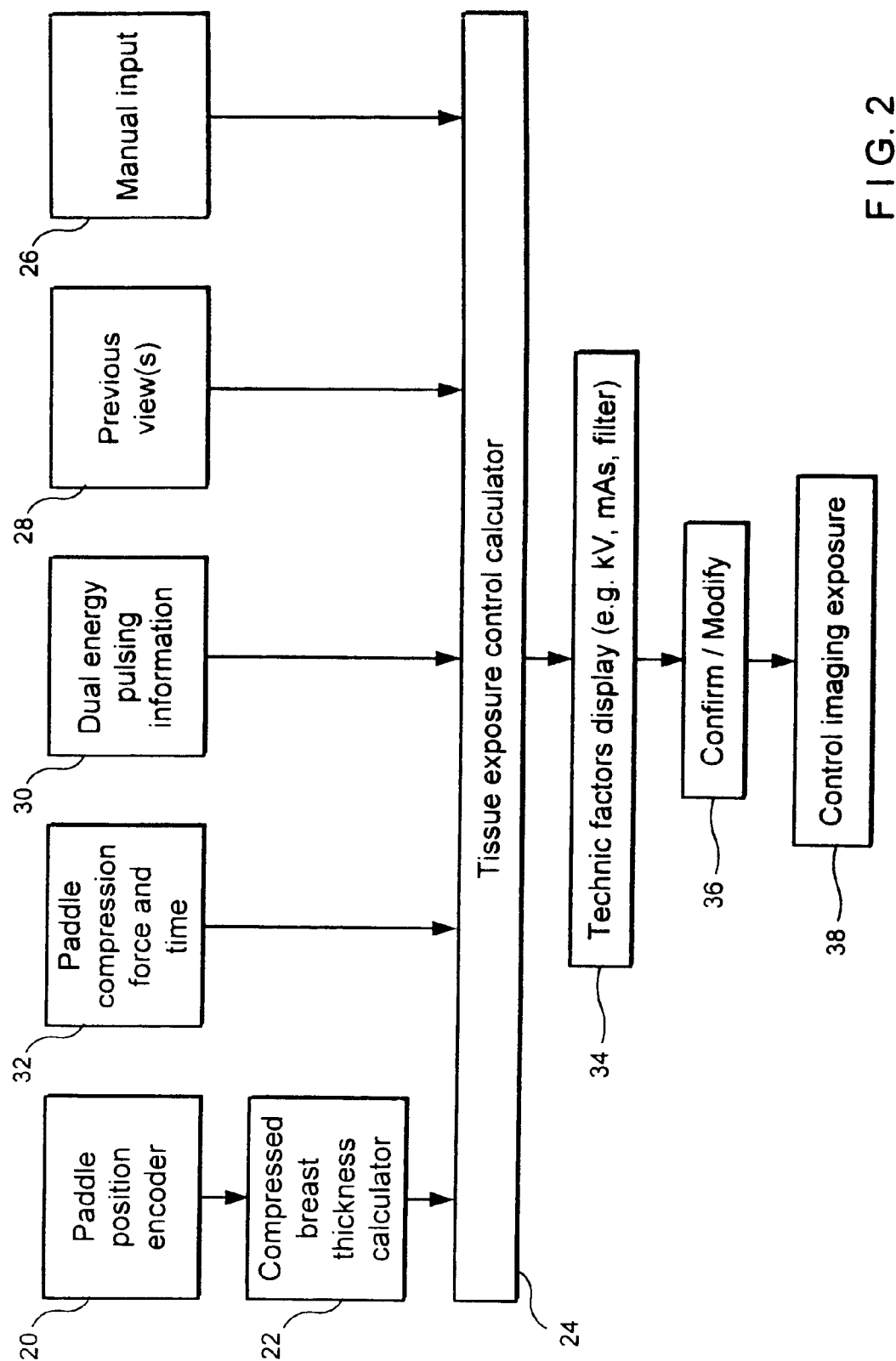
FIG. 2 is a flow chart illustrating processes of estimating and using tissue exposure control in a mammography system.

Referring to FIG. 1, a mammography system currently available from the common assignee under the trade name Selenia except for the new features described herein, comprises a stand 10 supporting a C-arm 12 that can move up or down along stand 10, to a selected height, driven by motor(s) controlled by a health professional operating the system. C-arm 12 carries an x-ray tube at an upper end 12a, a breast tray 12b at a lower end. Tray 12b covers a flat panel x-ray image receptor 12c, spaced from the tray by a focused anti-scatter grid 12d (which may be retractable so that it can be removed from the space between tray 12b and receptor 12c). C-arm 12 also carries a compression paddle 12e that is between source 12a and breast tray 12b and is motorized to move away from tray 12b so a patient's breast can be fitted between tray 12b and paddle 12e, and closer to tray 12b so the patient's breast can be compressed and immobilized. The movement of paddle 12e is motorized and controlled by the health professional. Different size paddles 12e can be fitted to suit different breast sizes for best compression. In addition, the health professional can move paddle 12 along the width of tray 12b to a position in which paddle 12e matches the position of a breast that is not centered on tray 12b, as in the Selenia system currently offered by the common assignee. The system further includes other components, such as a control station 14 comprising interface devices such a keyboard 14a and trackball 14b, a display screen 14c, and control and image processing facilities.

In order to carry out tissue exposure control, the currently available Selenia mammography system is modified to incorporate the equipment and process steps illustrated in FIG. 2. In particular, a paddle position encoder 20 measures the position of paddle 12e relative to tray 12b as the health professional positions, compresses and immobilizes the patient's breast for imaging. The thickness of the immobilized breast can be measured or estimated in other ways instead. For example, the final position of paddle 12e can be measured in some way, e.g. mechanically or optically or in some other way. The thickness of the immobilized breast may be measured or estimated directly in any one of a number of ways. A calculator 22, which can be implemented by suitably programming the processing unit 14 (FIG. 1) calculates the thickness of the compressed and immobilized breast on the basis of the output of encoder 20, or some other means for measuring breast thickness indicators, and provides information about breast thickness for a tissue exposure control calculator 24, which again can be implement through such programming.

To estimate technic factors, calculator 24 also relies on information about the x-ray density of the breast. Such information can come from one or more different sources. One example is manual input 26, e.g., keyboard 14a (FIG. 1), through which the health professional can input information characterizing the density of the breast. For example, the system can present the health professional with three choices—fatty, normal, and dense—and the health professional can make the appropriate choice based on any one or more factors such as physical examination of the breast, information from previous views in the same examination or taken at a much earlier time, or other information about the patient. Another example of a source of information about breast density is previous x-ray images (views) of the patient's breast or breasts. A previous view can be one taken at any earlier time, either in the same visit of the patient or at a previous visit. Information about density can be derived from the previous view(s) by the health professional, or it can be derived automatically—by measuring the overall density of a previous x-ray image and perhaps knowing the technic factors used to take it. If actually measured, the density information from the previous view(s) can be provided to calculator 24 manually or automatically, through a connection from the measuring device to calculator 24. Another source of density information is a dual energy arrangement 30 that pulses the immobilized breast with a low dose x-ray energy at each of two different energies, e.g. sequentially, and the measurements of x-rays with receptor 12c (FIG. 1) at each of the energies are used in a known process, similar to that used in bone densitometry, to estimate breast density and automatically or manually provide the estimate to calculator 24. X-ray tube 12a can be used for such dual energy process, using two different x-ray filters to emit x-rays at the appropriate to different energies or energy bands. Yet another source of information about breast density can be an arrangement 32 that measures the force with which paddle 12e compresses the breast and the time such force acts from the start of compression until the breast is immobilized for imaging, and supplies such force/time information to calculator 24, manually automatically.

Calculator 24 can be implemented as look-up table that in effect has an entry for each of a number of combinations of breast thickness and breast density values. The initial values of the entries can be estimated by actual tests, in essence a trial-and-error process, or in some other way. Calculator 24 provides its output to technic factor display 34, which can be display 14c (FIG. 1), at which the health professional can see the automatically estimated factors such as one or more of kV, mAs, filter, time, etc. An entry device, which can be keyboard 14a, allows the health professional to confirm or modify the automatically estimated parameters, and control 38 (which can be a part of unit 14 of FIG. 1) uses the resulting final tissue exposure control technic factors for an imaging x-ray exposure.

The examples disclosed in this patent specification refer to compressing and immobilizing the breast before determining technic factors and imaging. However, alternatives are contemplated in which the breast need not be compressed before imaging; the breast may be simply supported in some manner, such as by a breast tray, or may be suspended in some manner between an x-ray source and an image receptor. In such a case, the breast thickness and density information can come from different sources, such as measurements or estimates of the thickness of the uncompressed breast, or an average of the thickness of the breast portion that will be imaged, of the thickness of the part that is of particular interest for imaging. The density information may come from the health professional, or from prior x-ray images of the breast, or from some other source. The same alternative of imaging the uncompressed breast applies to the other two features discussed below—tomosynthesis and selecting a reduced field of view image for transmission and/or storage—where the alternative dispenses with compression but otherwise conforms to the description below.

Another feature of the mammography system disclosed here is tomosynthesis that to both allows a large field of view and the use of a focused anti-scatter grid. As illustrated in FIG. 3, anti-scatter grid 12d is focused to allow the passage of x-rays along paths 40 that emanate from the focal spot of x-ray source 12a and to suppress (scattered) x-rays that travel along other paths. If such a grid changes its orientation relative to the x-ray source, it would undesirably suppress x-rays that it should be passing. Such change in orientation would result if x-ray tube 12e moves in a direction transverse to the x-ray beam it emits while grid 12d and detector 12c remain stationary. In addition, such motion would reduce the field of view, so a portion of the breast projected on the receptor in one position of the moving source may fall outside the receptor outline at another position of the source.

FIG. 4 illustrates an arrangement that overcomes these deficiencies of a known proposal. In FIG. 4, x-ray tube 12a and the combination of anti-scatter grid 12d and receptor 12c rotate as a unit while a compressed and immobilized breast remains between them and in the path of x-rays emitted from tube 12a and impinging on receptor 12c. Anti-scatter grid 12d remains focused on the focal spot of tube 12a, and the effective field of view does not change with angular position of the source-receptor unit. In the currently offered Selenia unit, source 12a and grid I 2d and receptor 12c rotate as a unit, also together with compression paddle 12e and breast tray 12b, so a modification is needed to achieve the geometry of FIG. 4. This modification involves decoupling a means to compress and immobilize the breast from motion of tube 12a, grid 12d and receptor 12c. For example, this can be done by removing compression paddle 12e and compressing and immobilizing the breast between compression paddles 44 that are appropriately positioned relative to the center of rotation of tube 12a but do not rotate with tube 12a. as illustrated in FIG. 4. As an alternative to rotation, one or both of tube 12a and receptor 12c can translate relative to the breast immobilized between paddles 44. In such case, focused grid 12d can be decoupled from receptor 12c and allowed to remain focused at tube 12a, or a different grid can be used that is not focused or is less focused, and/or the motion of tube 12a and/or receptor 12c can be over a more limited path. Discrete x-ray images of the breast are taken at each of a number of different positions of tube 12e relative to the breast. The image data is used for tomosynthesis through the application of known image processing methods.

An important advantage of the example of FIG. 4 is that it allows imaging at relatively large angles between the extreme rotational or translational positions of x-ray tube 12a as compared with known systems.

Yet another feature of the mammography system disclosed here is to transmit and store only a portion of the field of view. With a relatively large field-of-view receptor 12c, such as used in the Selenia system (24×29 cm), typically the image of the breast lies within a rectangle that is smaller than the field of view, as illustrated in FIG. 5, where the image 46 of a breast is within a notional rectangular outline 48 (reduced field of view) that is much smaller than the field of view 50 of receptor 12c. The area of field of view 50 that is outside the reduced filed of view area 48 may contain little or no information about the breast. To save on transmitting and storing the breast image, only the information within the reduced field of view 48 may be used, and any information outside outline 48 can be discarded. If there is any significant information outside outline 48, only that information can be attached to the information for the image portion inside outline 48.

One way to select the position and size of outline 48 is to rely on the selection of the size and position of compression paddle 12e that the health professional has made. As earlier noted, the currently offered Selenia system allows the health professional to select both the size of a paddle and, at least for some paddles, also the position of the paddle relative to receptor 12c, so as to match the size and position on receptor 12c of the breast being x-rayed. The size and position of paddle 12e can be automatically determined, and the result used to in effect crop the resulting breast image before transmitting and/or storing and/or formatting it for transmission or storage, for example according to DICOM standards. Alternatively, the size and position of the breast in the image can be found through image analysis, such as analysis involving edge detection, and the size and position of outline 48 can be found in this manner. Still alternatively, the size and position of outline 48 may be entered by the health professional, e.g., through keyboard 14a, based on viewing the image displayed on monitor 14c. Or, a combination of said methods can be used, e.g., an automatic determination based on one or both of image analysis and paddle selection, followed with a presentation of a recommended outline 48 displayed to the health professional together with the entire image, for confirmation or modification by the health professional.

FIG. 6 illustrates an arrangement for providing a reduced field of view image. A compression paddle size and position encoder incorporated in C-arm 12 or elsewhere in association with the means for mounting and moving paddle 12e provides information about the paddle 12e that the health professional has selected, and about the position of the paddle's projection on receptor 12c. A manual input provides information entered by the health professional, which can be similar to that provided by encoder 52 or can be information regarding which of several rectangles within the entire breast image encompasses the breast, or what arbitrary rectangle can encompass the breast on the image. An image analyzer 56 provides information about the area in the overall image occupied by the breast. A calculator 58 uses the information from one or more of units 52, 54 and 57 to calculate the size and position of a reduced field of view that still encompasses the breast, and the calculation is displayed at 60, e.g., as an outline 48 in an image such as illustrated in FIG. 5, for the health professional to confirm or modify, e.g. through manual entries. The result is a finalized reduced field of view image at 62 that can be used for further processing, for transmission, and/or storage. While a rectangular outline 48 has been discussed above, in fact outline 48 can have other suitable shapes.

The invention claimed is:

1. A system selectively operable in each of a tomosynthesis mode and a mammography mode, comprising:

an x-ray tube, an x-ray imaging receptor, and a breast immobilizer, wherein (i) the x-ray tube and x-ray imaging receptor are decoupled from the breast immobilizer when the system is operating in said tomosynthesis mode but (ii) the tube, receptor and immobilizer are mounted to move as a unit between different mammography imaging positions when the system is operating in said mammography mode; and an anti-scatter grid mounted between the breast immobilizer and the x-ray imaging receptor;

said anti-scatter grid remaining between the source and the receptor to suppress x-ray scatter both when the system is operating in said mammography mode and when the system is operating in said tomosynthesis mode;

said system being configured to operate selectively in:

(i) said tomosynthesis mode in which the x-ray source selectively emits imaging x-rays from different tomosynthesis imaging positions that are at different angles relative to the breast immobilizer, to thereby obtain a multiplicity of projection tomosynthesis images Tp related to respective ones of said different tomosynthesis imaging positions, and (ii) said mammography mode in which the x-ray source emits imaging x-rays while the x-ray source, the x-ray imaging receptor and the breast immobilizer do not move with respect to each other to thereby obtain a projection mammogram Mp related to one of said mammography imaging positions.

2. The system as in claim 1 in which:

said breast immobilizer comprises a breast tray and a compression paddle; and said compression paddle is mounted for movement along a width of the breast tray to a position matching the position of a patient's breast that is between the compression paddle and the breast tray but is not centered on the breast tray.

3. The system as in claim 1 in which in which the x-ray source rotates relative to the breast immobilizer between different ones of said tomosynthesis imaging positions.

4. The system as in claim 1 in which in which the imaging receptor changes angular orientation relative to the breast immobilizer as the source moves between said different tomosynthesis imaging positions.

5. The system as in claim 1 in which in which the x-ray source and the imaging receptor rotate as a unit relative to the breast immobilizer between said different tomosynthesis imaging positions.

6. The system as in claim 1 in which including a tissue exposure control calculator configured to receive information regarding a density of a patient's breast in said breast immobilizer derived from said imaging receptor and to use said information to calculate x-ray exposure factors for imaging said breast with said imaging x-rays.

7. The system as in claim 1 in which including a tissue exposure control calculator configured to receive information regarding a thickness of a patient's breast in said breast immobilizer derived from a breast thickness encoder and to use said information to calculating x-ray exposure factors for imaging the breast with said imaging x-rays.

8. The system as in claim 1 in which in which said antiscatter grid is a two-dimensional focused grid.

9. The system as in claim 1 in which in which said antiscatter grid comprises a two-dimensional array of open cells oriented to point at a focal spot of the x-ray source.

* * * * *